United States Patent [19]

Hughes et al.

[11] Patent Number: 5,628,935

[45] Date of Patent: May 13, 1997

[54] PHOTOCHROMIC SPIRONAPHTHOPYRAN COMPOUNDS

[75] Inventors: Frank J. Hughes, Edina, Minn.; Edward A. Travnicek, Coral Springs, Fla.

[73] Assignee: Vision-Ease Lens, Inc., Brooklyn Center, Minn.

[21] Appl. No.: 331,281

[22] Filed: Oct. 28, 1994

[51] Int. Cl.$^6$ .................. C07D 311/92; C07D 413/00
[52] U.S. Cl. .................. 252/589; 252/586; 351/163; 524/110; 544/150; 544/375; 546/282.7; 549/389; 106/170.12
[58] Field of Search .................. 549/389; 524/110; 351/163; 544/150, 375; 546/269; 252/589, 586

[56] References Cited

U.S. PATENT DOCUMENTS 5,532,361  7/1996  Allegrini et al. .................. 544/70

*Primary Examiner*—Amelia A. Owens
*Attorney, Agent, or Firm*—Kinney & Lange, P.A.

[57] ABSTRACT

A naphthopyran compound represented by the formula:

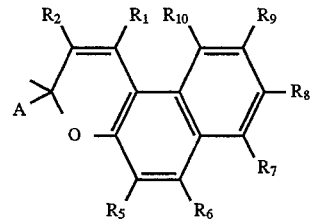

wherein $R_1$, $R_2$, $R_5$, $R_6$, $R_7$, $R_8$, $R_9$, and $R_{10}$ are each selected from the group consisting essentially of hydrogen, a stable organic radical, a heterocyclic group, a halogen, a nitrogen-substituted group, and a nitrogen-substituted ring compound and wherein A is a substituted divalent aromatic radical that includes substituents selected from the group consisting essentially of hydrogen and the stable organic radical.

25 Claims, No Drawings

PHOTOCHROMIC SPIRONAPHTHOPYRAN COMPOUNDS

BACKGROUND OF THE INVENTION

The present invention generally relates to naphthopyran compounds. More specifically, the present invention relates to photochromic spironaphthopyran compounds and to articles made of photochromic spironaphthopyran compounds.

Photochromism generally concerns the ability of a compound to reversibly change color under different light conditions. One particular type of photochromic phenomenon concerns the reversible change in color of a compound from an original color to a different color when the compound is exposed to a source of ultraviolet radiation, such as solar radiation or light radiated from a mercury or xenon lamp. The photochromic compound fades to the original color within a period of time after the photochromic compound is isolated from the ultraviolet radiation, such as by placing the compound in a dark room.

Various products, including optical lenses, incorporate the principal of photochromism. For example, photochromic compounds, such as naphthopyrans, are incorporated into plastic ophthalmic lenses to effect color changes in the lenses when the lenses are exposed to particular lighting conditions. Additionally, different photochromic compounds may be blended together to create a color effect that is different from respective color effects of the individual photochromic compounds. As an example, a first photochromic compound that turns orange or red when activated by light and a second photochromic compound that turns blue when activated by light may be blended together to form a photochromic mixture that produces a shade of gray when activated by light.

Several types of photochromic compounds have been reported which exhibit changes in color when exposed to ultraviolet light. One particular class of photochromic compounds includes the 3,3-disubstituted naphthopyrans. One specific group of 3,3-disubstituted naphthopyrans includes the 3H-naphtho[2,1b]pyrans. The color response of the 3H-naphtho[2,1b]pyrans to ultraviolet light extends to purple, red, orange, or yellow, depending upon the composition and structure of the particular 3H-naphtho[2,1b] pyrans. A general expression of the 3H-naphtho[2,1b]pyrans is provided in graphical formula I:

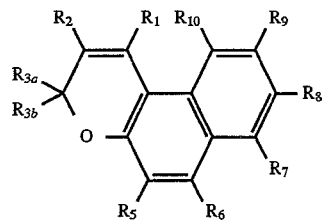

I where $R_{3a}$ and $R_{3b}$ are substituents attached to the pyran ring at the position indicated.

U.S. Pat. No. 3,567,605 to Becker describes chromenes and chromene derivatives which are photochromic at relatively low temperature. The Becker patent also describes chromenes and chromene derivatives which are photochromic at room temperature, such as diphenyl-3H-naphtho[2,1b]pyran, where $R_{3a}$ and $R_{3b}$ of formula I are each phenyl groups.

U.S. Pat. No. 4,931,221 to Heller et al. describes additional photochromic compounds, including 3H-naphtho[2,1b]pyrans represented by formula I, where $R_{3a}$ and $R_{3b}$ are cyclopropyl radicals and where any of various substituents are included on the naphtho portion of the naphthopyran rings. Heller reports that the 3H-naphtho[2,1b]pyrans which include cyclopropyl radicals exhibit a larger bathychromic shift in the visible spectrum, as compared to 3H-naphtho[2,1b]pyrans which include alkyl groups or a spirocycloalkyl group in place of the cyclopropyl radicals.

U.S. Pat. No. 5,066,818 to Gemert et al. discloses additional photochromic compounds generally meeting graphical formula I. The Gemert patent reports a range of decolorization rates associated with the 3H-naphtho[2,1b]pyrans.

U.S. Pat. No. 5,106,998 to Tanaka et al. describes compounds in which $R_{3a}$ and $R_{3b}$ of graphical formula I are alkyl groups. Tanaka reports several fade times and maximum absorption wavelengths associated with the compounds.

U.S. Pat. No. 5,238,981 to Knowles describes naphthopyran compounds of graphical formula I in which $R_{3a}$ and $R_{3b}$ are each selected from a group of organic radicals that include phenyl and naphthyl. Various potential substitutions on the naphtho portion of the naphthopyrans ring are taught, including an 8-methoxy substitution. Knowles states that number eight carbon atom substitutions, such as the 8-methoxy substitution, cause a bathychromic shift in the visible spectrum associated with activated forms of the 3H-naphtho[2,1b]pyrans and in the ultraviolet spectrum of unactivated forms of the 3H-naphtho[2,1b]pyrans.

U.S. Pat. No. 5,244,602 to Van Gemert and U.S. Pat. No. 5,274,132 to Van Gemert each describe 3H-naphtho[2,1b] pyrans of graphical formula I that include various radical substitutions at the $R_{3a}$ and $R_{3b}$ positions. Each of these Van Gemert patents also claim to achieve bathychromic shifts in the visible spectrum associated with the 3H-naphtho[2,1b] pyrans.

Another class of photochromic compounds include spironaphthopyrans, as expressed in graphical formula II:

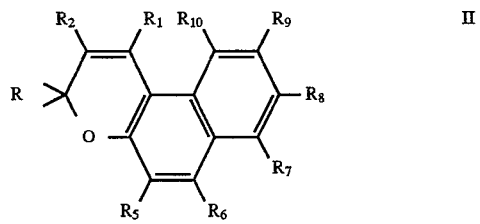

II

In formula II, $R_3$ is attached to the pyran ring by a spiro carbon, which is a single carbon atom that is shared by two separate rings. Compounds with a single carbon atom that is common to two separate rings are called spiro compounds. Very few naphthopyrans have been disclosed in which the carbon in the number 3 position of the naphthopyran ring is a spiro carbon.

U.S. Pat. No. 4,826,977 to Heller describes a naphthopyran of formula II where $R_3$ is the adamantyl group. Another patent, U.S. Pat. No. 4,980,089 to Heller, teaches a naphthopyran of formula II where $R_3$ may be a bicyclic norcamphane group, a tricyclodecane group, or derivatives of either the norcamphane group or the tricyclodecane group.

Additionally, U.S. Pat. No. 5,106,998 to Tanaka et al. describes pyran compounds, such as that of graphical formula II, in which $R_3$ is either a norbornylidene radical or a bicyclo[3,3,1]9-nonylidene radical. Tanaka reports several fade times and maximum absorption wavelengths associated with various naphthopyrans that include either the norbornylidene or the bicyclo[3,3,1]9-nonylidene radical.

SUMMARY OF THE INVENTION

The present invention includes a naphthopyran compound represented by the formula:

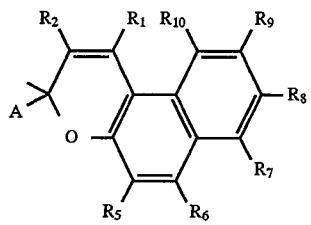

wherein $R_1$, $R_2$, $R_5$, $R_6$, $R_7$, $R_8$, $R_9$, and $R_{10}$ are each selected from the group consisting essentially of hydrogen, a stable organic radical, a heterocyclic group, a halogen, a nitrogen-substituted group, and a nitrogen-substituted ring compound. Additionally, A is a substituted divalent aromatic radical that includes substituents selected from the group consisting essentially of hydrogen and the stable organic radical. The present invention further includes a photochromic article comprising a host material and a photochromic amount of a naphthopyran compound and a method of making a naphthopyran.

DETAILED DESCRIPTION OF THE PREFERRED EMBODIMENTS

Novel compounds have been discovered which enable high wavelength activation and deep coloring; which have acceptable fade rates and which produce colors on activation that are capable of being blended with blue-producing photochromic compounds to produce remarkably pleasing gray colors when the blends are activated by ultraviolet radiation. The novel naphthopyran compounds of the present invention may be generally represented by graphic formula III as follows:

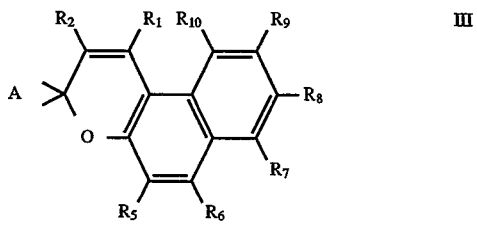

III

For purposes of the present application, including the description and the claims, it is to be understood that graphical formula III includes all structural isomers of the compounds represented by graphical formula III.

A variety of substituents may be placed on the pyran and the naphtho portion of the spiro naphthopyrans of the present invention. For example, the positions represented in graphic formula III by $R_1$, $R_2$, $R_5$, $R_6$, $R_7$, $R_8$, $R_9$, and $R_{10}$, respectively, may be filled with hydrogen; a stable organic radical, such as alkyl, alkoxy, phenyl, naphthyl, cycloalkyl, furyl, alkoyl, alkoyloxy, aroyl, aroyloxy; a heterocyclic group; a halogen; a nitrogen-substituted group, such as amino or nitro; or a nitrogen-substituted ring compound, such as morpholino, piperidino, or piperazino.

Also in graphic formula III, the position represented by A is filled by a substituted divalent aromatic radical. The substituents of the divalent aromatic radical may be hydrogen or a stable organic radical such as alkyl, alkoxy, phenyl, naphthyl, cycloalkyl, furyl, alkoyl, alkoyloxy, aroyl, or aroyloxy. Additionally, the substituents of the substituted divalent may also be substituted with alkyl, alkoxy, phenyl, naphthyl, cycloalkyl, furyl, alkoyl, alkoyloxy, aroyl, or aroyloxy.

The compounds represented by graphic formula III are derivatives of aryl chromenes known as spironaphthopyrans.

These inventive spironaphthopyran compounds exhibit a surprising and highly desirable bathychromic shift of the maximum activated wavelength. The bathychromic shift exhibited by the inventive spironaphthopyran compounds provides photochromic species which turn orange, reddish-orange, or red when activated by an ultraviolet radiation source.

It has been found desirable to produce photochromic compounds with maximum activated wavelengths approaching and even exceeding 500 nanometers. Photochromic compounds with maximum activated wavelengths near or above 500 nanometers change from original states of color to deep shades of orange, reddish-orange, or red when activated by ultraviolet light. The colored forms of the activated photochromic compounds fade to the original, unactivated color states at ambient temperatures when isolated from the ultraviolet light. As used in this disclosure, "intense photochromes" refers to photochromic compounds that turn deep shades of orange, reddish orange, or red when activated.

The inventive naphthopyrans represented by graphic formula III, especially the intense photochromes, exhibit a deeper color and a larger bathychromic shift in the visible spectrum of the activated state as compared to existing naphthopyrans. Indeed, the inventive naphthopyrans represented by graphic formula III, especially the intense photochromes, approach a maximum activated wavelength of 500 nanometers; exhibit deep shades of orange, reddish-orange, or red; and include an acceptable fade characteristic. Surprisingly, one preferred naphthopyran of the present invention actually exceeds the 500 nanometer maximum activated wavelength level.

Acceptable spironaphthopyran compounds of the present invention have a maximum activated wavelength when dissolved in either cyclohexane or chloroform of at least about 438 nanometers. More preferably, the inventive spironaphthopyrans have a maximum activated wavelength when dissolved in cyclohexane or chloroform of at least about 465 nanometers. Still more preferably, the spironaphthopyrans of the present invention have maximum activated wavelengths when dissolved in cyclohexane or chloroform of at least about 490 nanometers.

The intense spironapthopyrans of the present invention may be blended with one or more other photochromic compounds having maximum activation wavelengths different from that of the inventive intense photochromes to make photochromic mixtures. Preferably, the other photochromic compounds turn colors other than orange, reddish orange and red when activated with ultraviolet light. In one embodiment, one or more of the inventive intense photochromes is preferably blended with another photochromic compound, which has a different maximum activation wavelength and which turns blue when activated with ultraviolet light, to make the photochromic mixture. It has been discovered that photochromic mixtures that include blends of the inventive intense photochromes and blue-turning photochromic compounds change to pleasing, desirable, intense shades of gray when activated by ultraviolet light, such as that present in sunlight. The inventive spironaphthopyrans, alone, or the photochromic mixtures may be desirably applied as coatings to, or incorporated within, articles, such as conventional synthetic plastic materials often used for optical elements.

Compounds of graphic formula III above may be prepared by reacting a suitable ketone precursor with a metal salt of an alkyne to make an intermediate. The intermediate is then reacted with either an unsubstituted naphthol or a substituted naphthol in the presence of a catalyst. The resultant material is then purified by recrystallization, column chromatography, or a combination of recrystallization and column chromatography.

Suitable ketone precursors may be represented by graphic formula IV:

where the position represented by A is filled by the substituted divalent aromatic radical described with reference to graphic formula III. As already indicated, the substituents of the substituted divalent aromatic radical, may be hydrogen, or a stable organic radical such as alkyl, alkoxy, phenyl, naphthyl, cycloalkyl, furyl, alkoyl, alkoyloxy, aroyl, or aroyloxy. Some examples of suitable ketone precursors consistent with graphical formula IV are shown below:

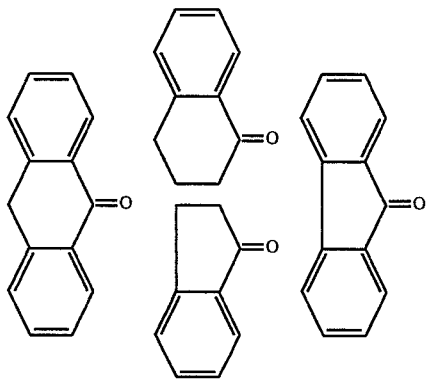

The metal salt of the alkyne is preferably lithium acetylide and the organic solvent is preferably tetrahydrofuran. The naphthol is preferably either an unsubstituted 2-naphthol or a substituted 2-naphthol. The catalyst is preferably a catalytic amount of p-toluenesulfonic acid.

One particularly effective naphthopyran compound, consistent with graphic formula III, is 8-methoxyspiro(3H-naphtho[2,1-b]pyran-2,9'-fluorene), which is represented by graphic formula V:

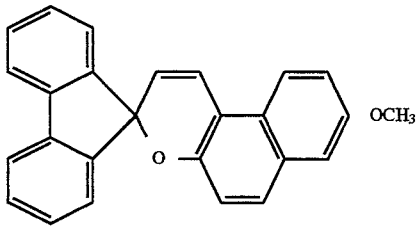

This compound has an activated maximum wavelength of absorption, when dissolved in chloroform, of about 492 nanometers when irradiated with ultraviolet light. Additionally, when activated by ultraviolet light, the 8-methoxyspiro(3H-naphtho[2,1-b]pyran-2,9'-fluorene) turns a deep shade of orange. Furthermore, the 8-methoxyspiro(3H-naphtho[2,1-b]pyran-2,9'-fluorene) blends with blue-turning photochromic compounds, such as substituted spiroindolino naphthoxazine, to advantageously make one of the photochromic compound blends that changes to a desirable, intense shade of gray when activated by ultraviolet radiation.

Compounds represented by graphic formula III may be used in many applications of plastic substrates. For example, compounds represented by graphic formula III may be incorporated into a host material that is applied to an article.

Also, compounds represented by graphic formula III may be combined with the host material to make the article. Additionally, compositions that contain one or more of the photochromic compounds represented by graphic formula III, such as the previously mentioned photochromic mixtures, may be incorporated into the host material. The combination of the composition and host material, as already noted, may be applied to or used to make the article. Also, compounds represented by graphic formula III and compositions containing one or more compounds represented by graphic formula III may be incorporated into a coating material that may be applied to the host material.

In another example, the article may be formulated for use as a coating for a suitable substrate. Polymerized organic materials, such as synthetic polymerized plastic often used to make optical elements, are examples of the host material. Examples of the article include optical elements, such as plano and ophthalmic lenses.

Non-exhaustive illustrations of suitable synthetic polymerized plastics include polyacrylate, polycarbonate, polyvinyl alcohol, polyvinyl acetate, polyvinyl chloride, polyurethane, cellulose ester and bis-polyol (allyl carbonate) monomer-based polymer. As used in this disclosure, the term bis-polyol (allyl carbonate) monomer and similar phrases are intended to mean and include the named monomer or prepolymer and any related monomer series contained therein. Some non-limiting examples of bis-polyol (allyl carbonate) monomers include ethylene glycol bis(allyl carbonate), diethylene glycol bis(2-methylallyl carbonate), diethylene glycol bis(allyl carbonate), propylene glycol bis(2-ethylallyl carbonate), 1-3-propanediol bis(allyl carbonate), 1,3-butanediol bis(allyl carbonate), 1,4-butanediol bis(2,bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

The amount of a particular one of the compounds represented by graphic formula III, or a particular composition containing one of the compounds represented by graphic formula III, that is incorporated into the host material or the coating material is defined, for purposes of this disclosure, as the photochromic amount. The photochromic amount is not critical, provided that a sufficient amount to produce a photochromic effect perceptible to the human eye is used. The photochromic amount often depends on the desired intensity of the color on activation of the particular inventive naphthopyran and on the method of incorporation or application of the particular inventive naphthopyran. Typically, the photochromic amount incorporated into or applied to the host material or incorporated into the coating material ranges from about 0.01 to about 20 percent by weight, based on the weight of the host material or the weight of the coating material, as applicable.

The present invention is more particularly described in the following examples which are intended as illustrations only since numerous modifications and variations within the scope of the general formulation will be apparent to those skilled in the art.

EXAMPLE 1

Step 1

5.4 grams of 9-fluorenone were placed together with 5 grams of lithium acetylide in 250 milliliters of tetrahydrofuran and stirred for 72 hours. The 9-fluorenone served as the ketone precursor, which is subsequently referred to as compound K. The 9-fluorenone/lithium acetylide/ tetrahydrofuran mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in a solvent and the solvent solution was cooled to yield a recrystallized compound. Nuclear magnetic resonance (NMR) spectroscopy showed the recrystallized compound to be, 9,9 fluorenediyl propargyl alcohol, a relatively pure substituted propargyl alcohol.

Step 2

1.24 grams of 9,9 fluorenediyl propargyl alcohol, the substituted propargyl alcohol from Step 1, were mixed with 1.05 grams of 6-methoxy-2-naphthol in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in a solvent and the solvent solution was cooled to yield a recrystallized product. The recrystallized product was shown to be the following substituted 3H-naphtho[2,1-b]pyran, 8-methoxyspiro(3H-naphtho[2,1-b]pyran-3,9'-fluorene):

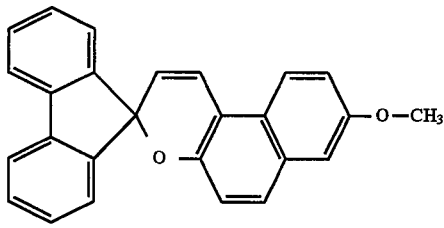

by nuclear magnetic resonance (NMR) spectroscopy. The substituted 3H-naphtho[2,1-b]pyran product, in subsequent examples, is referred to as compound P.

EXAMPLE 2

The procedure of Example 1 was repeated in Example 2 except that the compound K used in Example 2 was 1-tetralone; the substituted propargyl alcohol produced in Step 1 was other than 9,9 fluorenediyl propargyl alcohol; the amount of substituted propargyl alcohol from Step 1 that was used in Step 2 was 1.03 grams; and the product compound P was 8-methoxyspiro(3H-naphtho[2,1-b]pyran-3,1'-tetralone), the structure of which is as follows:

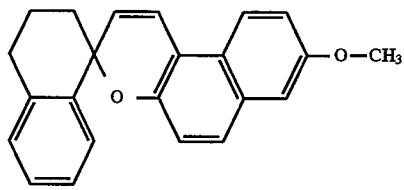

EXAMPLE 3

The procedure of Example 1 was repeated in Example 3 except that the compound K used in Example 3 was 6,7-dimethoxy-1-tetralone; the substituted propargyl alcohol produced in Step 1 was other than 9,9 fluorenediyl propargyl alcohol; the amount of substituted propargyl alcohol from Step 1 that was used in Step 2 was 1.39 grams; and the product compound P was 6',7'-dimethoxy-8-methoxyspiro (3H-naphtho[2,1-b]pyran-3,1'-tetralone), the structure of which is as follows:

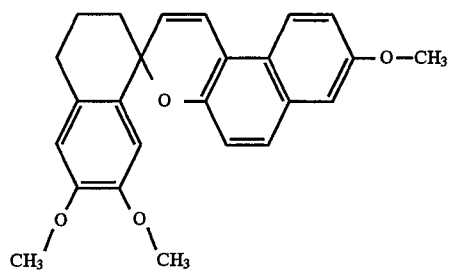

EXAMPLE 4

The procedure of Example 1 was repeated in Example 4 except that the compound K used in Example 4 was 7-methoxy-1-tetralone; the substituted propargyl alcohol produced in Step 1 was other than 9,9 fluorenediyl propargyl alcohol; the amount of substituted propargyl alcohol from Step 1 that was used in Step 2 was 1.21 grams; and the product compound P was 7'-methoxy-8-methoxyspiro(3H-naphtho[2,1-b]pyran-3,1'-tetralone), the structure of which is as follows:

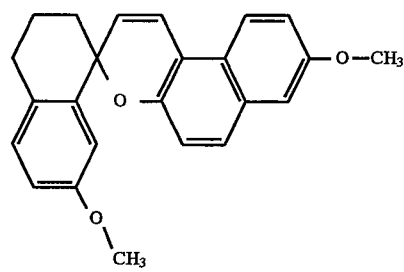

EXAMPLE 5

The procedure of Example 1 was repeated in Example 5 except that the compound K used in Example 5 was 2,3-diphenyl-1-tetralone; the substituted propargyl alcohol produced in Step 1 was other than 9,9 fluorenediyl propargyl alcohol; the amount of substituted propargyl alcohol from Step 1 that was used in Step 2 was 1.95 grams; and the product compound P was 2',3'-diphenyl-8-methoxyspiro (3H-naphtho[2,1-b]pyran-3,1'-tetralone), the structure of which is as follows:

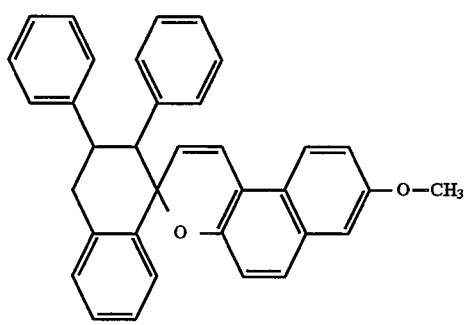

EXAMPLE 6

The procedure of Example 1 was repeated in Example 6 except that the compound K used in Example 6 was 2-methyl-1-tetralone; the substituted propargyl alcohol produced in Step 1 was other than 9,9 fluorenediyl propargyl alcohol; the amount of substituted propargyl alcohol from Step 1 that was used in Step 2 was 1.18 grams; and the product compound P was 2'-methyl-8-methoxyspiro(3H-naphtho[2,1-b]pyran-3,1'-tetralone), the structure of which is as follows:

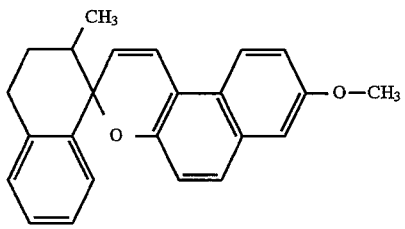

EXAMPLE 7

The procedure of Example 1 was repeated in Example 7 except that the compound K used in Example 7 was 2-methyl-1-indanone; the substituted propargyl alcohol produced in Step 1 was other than 9,9 fluorenediyl propargyl alcohol; the amount of substituted propargyl alcohol from Step 1 that was used in Step 2 was 1.03 grams, and the product compound P was 2'-methyl-8-methoxyspiro(3H-naphtho[2,1-b]pyran-3,1'-indan), the structure of which is as follows:

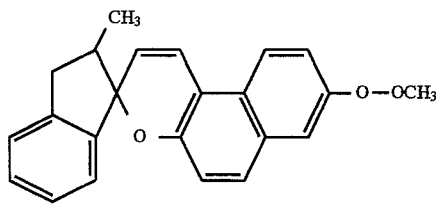

EXAMPLE 8

The procedure of Example 1 was repeated in Example 8 except that the compound K used in Example 8 was 2,3-diphenyl-1-indenone; the substituted propargyl alcohol produced in Step 1 was other than 9,9 fluorenediyl propargyl alcohol; the amount of substituted propargyl alcohol from Step 1 that was used in Step 2 was 1.85 grams, and the product compound P was 2',3'-diphenyl-8-methoxyspiro (3H-naphtho[2,1-b]pyran-3,1'-indene), the structure of which is as follows:

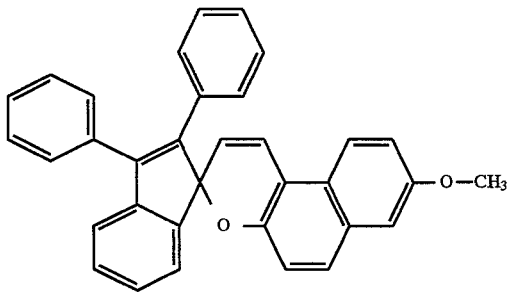

EXAMPLE 9

Step 1

5.4 grams of 9-fluorenone were placed together with 5 grams of lithium acetylide in 250 milliliters of tetrahydrofuran and stirred for 72 hours. The 9-fluorenone served as compound K, the ketone precursor. The 9-fluorenone/lithium acetylide/tetrahydrofuran mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material, was dissolved in a solvent and the solvent solution was cooled to yield a recrystallized compound. Nuclear magnetic resonance (NMR) spectroscopy showed the recrystallized compound to be, 9,9 fluorenediyl propargyl alcohol, a relatively pure substituted propargyl alcohol.

Step 2

1.24 grams of 9,9 fluorenediyl propargyl alcohol, the substituted propargyl alcohol, were mixed with 0.87 grams of 2-naphthol in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in a solvent and the solvent solution was cooled to yield a recrystallized product. The recrystallized product compound P was shown to be the following substituted 3H-naphtho[2,1-b]pyran, spiro(3H-naphtho[2,1-b]pyran-3, 9'-fluorene):

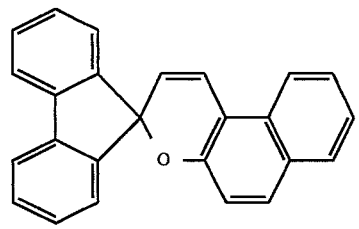

by nuclear magnetic resonance (NMR) spectroscopy.

EXAMPLE 10

The procedure of Example 9 was repeated in Example 10 except that the compound K used in Example 10 was 2,3-diphenyl-1-tetralone; the substituted propargyl alcohol produced in Step 1 was other than 9,9 fluorenediyl propargyl alcohol; the amount of substituted propargyl alcohol from Step 1 that was used in Step 2 was 1.95 grams; and the product compound P was 2',3'-diphenylspiro(3H-naphtho[2,1-b]pyran-3,1'-tetralone), the structure of which is as follows:

11

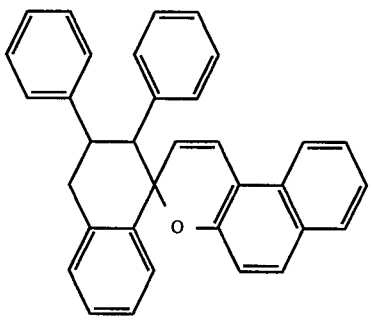

EXAMPLE 11

The procedure of Example 9 was repeated in Example 11 except that the compound K used in Example 11 was 2-methyl-1-tetralone; the substituted propargyl alcohol produced in Step 1 was other than 9,9 fluorenediyl propargyl alcohol; the amount of substituted propargyl alcohol from Step 1 that was used in Step 2 was 1.18 grams; and the product compound P was 2'-methylspiro(3H-naphtho[2,1-b]pyran-3,1'-tetralone), the structure of which is as follows:

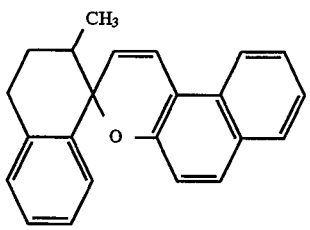

EXAMPLE 12

The procedure of Example 9 was repeated in Example 12 except that the compound K used in Example 12 was 2-methyl-1-indanone; the substituted propargyl alcohol produced in Step 1 was other than 9,9 fluorenediyl propargyl alcohol; the amount of substituted propargyl alcohol from Step 1 that was used in Step 2 was 1.03 grams; and the product compound P was 2'-methylspiro(3H-naphtho[2,1-b]pyran-3,1'-indan), the structure of which is as follows:

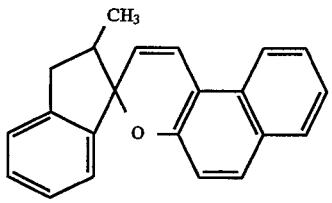

EXAMPLE 13

The procedure of Example 9 was repeated in Example 13 except that the compound K used in Example 13 was 2,3-diphenyl-1-indenone; the substituted propargyl alcohol produced in Step 1 was other than 9,9 fluorenediyl propargyl alcohol; the amount of substituted propargyl alcohol from Step 1 that was used in Step 2 was 1.85 grams, and the product compound P was 2',3'-diphenylspiro(3H-naphtho[2,1-b]pyran-3,1'-indene, the structure of which is as follows:

12

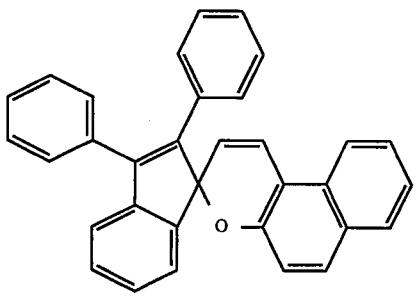

COMPARATIVE EXAMPLE 1

Step 1

Five grams of benzophenone were placed together with 5 grams of lithium acetylide in 250 milliliters of tetrahydrofuran and stirred for 72 hours. The benzophenone served as the ketone precursor. The benzophenone/lithium acetylide/tetrahydrofuran mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in a solvent and the solvent solution was cooled to yield a recrystallized compound. Nuclear magnetic resonance (NMR) spectroscopy showed the resultant material to be a relatively pure substituted propargyl alcohol, diphenyl propargyl alcohol.

Step 2

1.25 grams of the substituted propargyl alcohol, diphenyl propargyl alcohol, were mixed with a stoichiometric amount, 0.87 grams, of 6-methoxy-2-naphthol in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in a solvent and the solvent solution was cooled to yield a recrystallized product. The recrystallized product was shown to be a substituted 3H-naphtho[2,1-b]pyran, specifically, 3,3-diphenyl-8-methoxy-3H-naphtho[2,1-b]pyran, by nuclear magnetic resonance (NMR) spectroscopy.

DETERMINATION OF MAXIMUM ABSORPTION WAVELENGTH AND FADE TIME

Each of the photochromic compounds (compound P) formed in step 2 of Examples 1–13 and Comparative Example 1 were independently dissolved in separate containers of chloroform. Additionally, a purchased sample of 3,3-diphenyl-naphtho-3H[2,1-b]pyran, identified as Comparative Example 2, was dissolved in a separate container of chloroform.

Each of the chloroform-dissolved photochromic compounds of Examples 1–13 and Comparative Examples 1–2 were then irradiated with ultraviolet light with a maximum wavelength of 350 nanometers and were measured for maximum absorption wavelength $\lambda_{max}$. The fade time, $T_{1/2}$ was then determined for each of the irradiated compounds. The fade time for a particular chloroform dissolved photochromic compound is defined as the time interval, at room temperature (72° F.), for the absorbance of the activated form of the chloroform-dissolved photochromic compound to decrease to ½ of the maximum absorbance, after the photochromic compound is isolated from the activating source of ultraviolet light. The maximum absorption wavelength and fade time determined for each of the irradiated photochromic compounds of Examples 1–13 and Comparative Examples 1–2 are presented in Table 1:

TABLE 1

|  | $\lambda_{max}$ (Nanometers) | | $T_{1/2}$ (Seconds) |
| --- | --- | --- | --- |
|  | Cyclohexane | Chloroform | Chloroform |
| COMPOUND EXAMPLE | | | |
| 1 | 478 | 492 | 20 |
| 2 | 465 | 474 | 15 |
| 3 | * | 445 | * |
| 4 | ** | ** | ** |
| 5 | ** | 476 | 13 |
| 6 | ** | 468 | 1.2 |
| 7 | ** | 478 | 396 |
| 8 | ** | 512 | 64 |
| 9 | 438 | 445 | 10 |
| 10 | ** | ** | ** |
| 11 | ** | 444 | * |
| 12 | ** | ** | ** |
| 13 | ** | 454 | 35 |
| COMPARATIVE EXAMPLE | | | |
| 1 | 451 | 472 | 10 |
| 2 | 415 | 435 | 13 |

Comparative Example 2: Purchased 3,3-diphenyl-naphtho-3H[2,1-b]pyran
*Fades too fast to obtain readings
**Not Determined The values presented in Table 1 illustrate that the photochromic compound of Example 1, 8-methoxyspiro(3H-naphtho[2,1-b]pyran-3,9'-fluorene), has a longer maximum wavelength of activation than does the photochromic compound of Comparative Example 1, 3,3-diphenyl-8-methoxy-3H-naphtho[2,1-b]pyran. The Table 1 values also illustrate that the photochromic compound of Example 9, spiro(3H-naphtho[2,1-b]pyran-3,9'-fluorene), exhibits longer maximum wavelengths of activation than does the photochromic compound of Comparative Example 2, 3,3-diphenyl-naphtho-3H[2,1-b]pyran. The longer maximum wavelengths of activation exhibited by the inventive photochromic compounds of Examples 1–13 are desirable characteristics for substituted naphthopyran photochromic compounds.

Although the present invention has been described with reference to preferred embodiments, workers skilled in the art will recognize that changes may be made in form and detail without departing from the spirit and scope of the invention.

What is claimed is:

1. A naphthopyran compound represented by the formula:

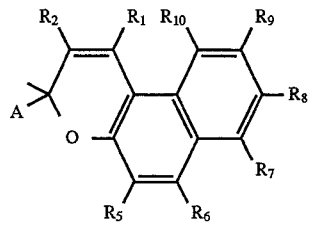

wherein, $R_1$, $R_2$, $R_5$, $R_6$, $R_7$, $R_8$, $R_9$, and $R_{10}$ are each selected from the group consisting essentially of hydrogen, a stable organic radical, a heterocyclic group, a halogen, a nitrogen-substituted group, and a nitrogen-substituted ring compound; and A is a substituted divalent aromatic radical, the substituents of the divalent aromatic radical selected from the group consisting essentially of hydrogen and the stable organic radical.

2. The naphthopyran compound of claim 1 wherein the stable organic radical is selected from the group consisting essentially of alkyl, alkoxy, phenyl, naphthyl, cycloalkyl, furyl, alkoyl, alkoyloxy, aroyl, and aroyloxy.

3. The naphthopyran compound of claim 1 wherein the nitrogen-substituted group is selected from the group consisting essentially of amino and nitro.

4. The naphthopyran compound of claim 1 wherein the nitrogen-substituted ring compound is selected from the group consisting essentially of morpholino, piperidino, and piperazino.

5. The naphthopyran compound of claim 1 wherein $R_1$, $R_2$, $R_5$, $R_6$, $R_7$, $R_8$, $R_9$, and $R_{10}$ are each selected from the group consisting essentially of hydrogen, alkyl, alkoxy, and cycloalkyl.

6. The naphthopyran compound of claim 5 wherein the substituents of the divalent aromatic radical are selected from the group consisting essentially of hydrogen, phenyl, naphthyl, alkyl, alkoxy, and cycloalkyl.

7. The naphthopyran compound of claim 1 wherein $R_1$, $R_2$, $R_5$, $R_6$, $R_7$, $R_8$, $R_9$, and $R_{10}$ are each selected from the group consisting essentially of hydrogen, C1–C2 alkyl, methoxy and ethoxy.

8. The naphthopyran compound of claim 7 wherein the substituents of the divalent aromatic radical are selected from the group consisting essentially of hydrogen, phenyl, naphthyl, alkyl, alkoxy, and cycloalkyl.

9. The naphthopyran compound of claim 1 wherein the naphthopyran compound is selected from the group consisting of 8-methoxyspiro(3H-naphtho[2,1-b]pyran-3,9'-fluorene), spiro(3H-naphtho[2,1-b]pyran-3,9'-fluorene), 8-methoxyspiro(3H-naphtho[2,1-b]pyran-3,1'-tetralone), 6',7'-dimethoxy-8-methoxyspiro(3H-naphtho[2,1-b]pyran-3,1'-tetralone), 7'-methoxy-8-methoxyspiro(3H-naphtho[2,1-b]pyran-3,1'-tetralone), 2',3'-diphenyl-8-methoxyspiro(3H-naphtho[2,1-b]pyran-3,1'-tetralone), 2'-methyl-8-methoxyspiro(3H-naphtho[2,1-b]pyran-3,1'-tetralone), 2'-methyl-8-methoxyspiro(3H-naphtho[2,1-b]pyran-3,1'-indan), 2',3'-diphenyl-8-methoxyspiro(3H-naphtho[2,1-b]pyran-3,1'-indene), 2',3'-diphenyl-8-methoxyspiro(3H-naphtho[2,1-b]pyran-3,1'-tetralone), 2'-methyl-8-methoxyspiro(3H-naphtho[2,1-b]pyran-3,1'-tetralone), 2'-methyl-8-methoxyspiro(3H-naphtho[2,1-b]pyran-3,1'-indan), and 2',3'-diphenyl-8-methoxyspiro(3H-naphtho[2,1-b]pyran-3,1'-indene).

10. A photochromic article comprising a host material and a photochromic amount of a naphthopyran compound, the naphthopyran compound represented by the formula:

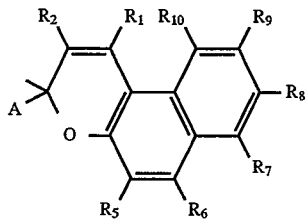

wherein, $R_1, R_2, R_5, R_6, R_7, R_8, R_9,$ and $R_{10}$ are each selected from the group consisting essentially of hydrogen, a stable organic radical, a heterocyclic group, a halogen, a nitrogen-substituted group, and a nitrogen-substituted ring compound; and A is a substituted divalent aromatic radical, the substituents of the divalent aromatic radical selected from the group consisting essentially of hydrogen and the stable organic radical.

11. The photochromic article of claim 10 wherein the stable organic radical is selected from the group consisting essentially of alkyl, alkoxy, phenyl, naphthyl, cycloalkyl, furyl, alkoyl, alkoyloxy, aroyl, and aroyloxy.

12. The photochromic article of claim 10 wherein the nitrogen-substituted group is selected from the group consisting essentially of amino and nitro.

13. The photochromic article of claim 10 wherein the nitrogen-substituted ring compound is selected from the group consisting essentially of morpholino, piperidino, and piperazino.

14. The photochromic article of claim 10 wherein $R_1, R_2, R_5, R_6, R_7, R_8, R_9,$ and $R_{10}$ are each selected from the group consisting essentially of hydrogen, alkyl, alkoxy, and cycloalkyl.

15. The photochromic article of claim 14 wherein the substituents of the divalent aromatic radical are selected from the group consisting essentially of hydrogen, phenyl, naphthyl, alkyl, alkoxy, and cycloalkyl.

16. The photochromic article of claim 10 wherein $R_1, R_2, R_5, R_6, R_7, R_8, R_9,$ and $R_{10}$ are each selected from the group consisting essentially of hydrogen, C1–C2 alkyl, methoxy and ethoxy.

17. The photochromic article of claim 16 wherein the substituents of the divalent aromatic radical are selected from the group consisting essentially of hydrogen, phenyl, naphthyl, alkyl, alkoxy, and cycloalkyl.

18. The photochromic article of claim 10 wherein the host material is made of a polymerized organic compound.

19. The photochromic article of claim 11 wherein the polymerized organic compound is selected from the group consisting essentially of polyacrylate, polycarbonate, polyvinyl alcohol, polyvinyl acetate, polyvinyl chloride, polyurethane, cellulose ester, and a polymer of bis-polyol (allyl carbonate) monomer.

20. The photochromic article of claim 10 wherein the naphthopyran compound is present in an amount of from about 0.01 to about 20 percent by weight, based on the weight of the host material.

21. The photochromic article of claim 10 wherein the article is an optical element.

22. The photochromic article of claim 10 wherein the optical element is a lens.

23. The photochromic article of claim 10 wherein the article is a coating for a substrate.

24. The photochromic article of claim 10, the article further comprising one or more additional photochromic compounds, the naphthopyran compound and the additional photochromic compounds having different maximum wavelengths of activation.

25. The photochromic article of claim 10 wherein the naphthopyran compound is selected from the group consisting of 8-methoxyspiro(3H-naphtho[2,1-b]pyran-3,9'-fluorene), spiro(3H-naphtho[2,1-b]pyran-3,9'-fluorene), 8-methoxyspiro(3H-naphtho[2,1-b]pyran-3,1'-tetralone), 6',7'-dimethoxy-8-methoxyspiro(3H-naphtho[2,1-b]pyran-3,1'-tetralone), 7'-methoxy-8-methoxyspiro(3H-naphtho[2,1-b]pyran-3,1'-tetralone), 2',3'-diphenyl-8-methoxyspiro(3H-naphtho[2,1-b]pyran-3,1'-tetralone), 2'-methyl-8-methoxyspiro(3H-naphtho[2,1-b]pyran-3,1'-tetralone), 2'-methyl-8-methoxyspiro(3H-naphtho[2,1-b]pyran-3,1'-indan), 2',3'-diphenyl-8-methoxyspiro(3H-naphtho[2,1-b]pyran-3,1'-indene), 2',3'-diphenyl-8-methoxyspiro(3H-naphtho[2,1-b]pyran-3,1'-tetralone), 2'-methyl-8-methoxyspiro(3H-naphtho[2,1-b]pyran-3,1'-tetralone), 2'-methyl-8-methoxyspiro(3H-naphtho[2,1-b]pyran-3,1'-indan), and 2',3'-diphenyl-8-methoxyspiro(3H-naphtho[2,1-b]pyran-3,1'-indene).

* * * * *

UNITED STATES PATENT AND TRADEMARK OFFICE
CERTIFICATE OF CORRECTION

PATENT NO. : 5,628,935

DATED : MAY 13, 1997

INVENTOR(S) : FRANK J. HUGHES, EDWARD A. TRAVNICEK

It is certified that error appears in the above-indentified patent and that said Letters Patent is hereby corrected as shown below:

On the title page, item [56]:
Under References Cited U.S. PATENT DOCUMENTS, insert the following references:

| | | | | | |
|---|---|---|---|---|---|
| AA | 3,567,605 | 03/02/71 | Becker | 204 | 158 |
| AB | 4,826,977 | 05/02/89 | Heller et al. | 544 | 70 |
| AC | 4,931,221 | 06/05/90 | Heller | 252 | 586 |
| AD | 4,980,089 | 12/25/90 | Heller | 252 | 586 |
| AE | 5,066,818 | 11/19/91 | Gemert et al. | 549 | 389 |
| AF | 5,106,998 | 04/21/92 | Tanaka et al. | 549 | 331 |
| AG | 5,238,981 | 08/24/93 | Knowles | 524 | 110 |
| AH | 5,244,602 | 09/14/93 | VanGemert | 252 | 589 |
| AI | 5,274,132 | 12/29/93 | VanGemert | 549 | 389 |
| AJ | 5,395,567 | 3/95 | VanGemert et al. | 252 | 586 |

UNITED STATES PATENT AND TRADEMARK OFFICE
CERTIFICATE OF CORRECTION

PATENT NO. : 5,628,935
DATED : MAY 13, 1997
INVENTOR(S) : FRANK J. HUGHES, EDWARD A. TRAVNICEK

It is certified that error appears in the above-indentified patent and that said Letters Patent is hereby corrected as shown below:

Under the [57] ABSTRACT, please delete the following formula:

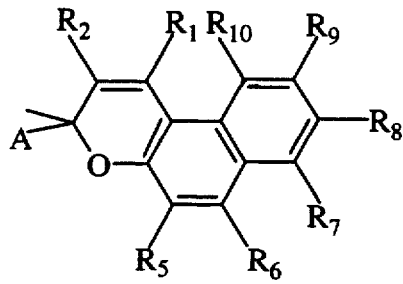

and insert under the [57] ABSTRACT, the following formula:

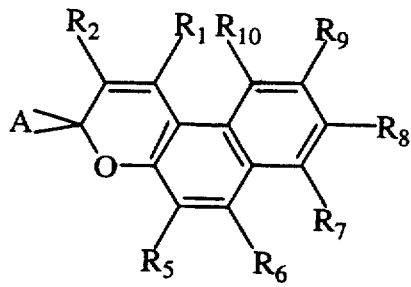

UNITED STATES PATENT AND TRADEMARK OFFICE
CERTIFICATE OF CORRECTION

Page 3 of 8

PATENT NO. : 5,628,935
DATED : MAY 13, 1997
INVENTOR(S) : FRANK J. HUGHES, EDWARD A. TRAVNICEK

It is certified that error appears in the above-indentified patent and that said Letters Patent is hereby corrected as shown below:

Col. 2, line 6, delete "spirocycloallcyl", insert --spirocycloalkyl--

Col. 3, lines 1-10, please delete the following formula:

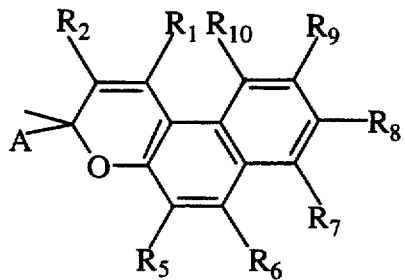

and insert the following formula under Col. 3, lines 1-10--

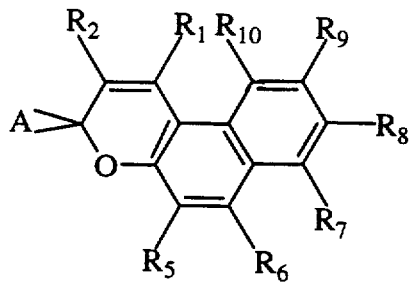

UNITED STATES PATENT AND TRADEMARK OFFICE
CERTIFICATE OF CORRECTION

PATENT NO. : 5,628,935
DATED : MAY 13, 1997
INVENTOR(S) : FRANK J. HUGHES, EDWARD A. TRAVNICEK

It is certified that error appears in the above-indentified patent and that said Letters Patent is hereby corrected as shown below:

Col. 3, line 34, delete "III", and insert --III-- immediately to the left of structure indicated below, as follows:

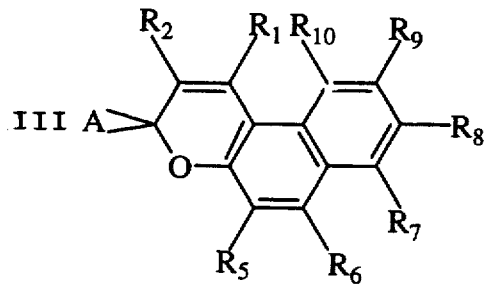

UNITED STATES PATENT AND TRADEMARK OFFICE
CERTIFICATE OF CORRECTION

PATENT NO. : 5,628,935
DATED : MAY 13, 1997
INVENTOR(S) : FRANK J. HUGHES, EDWARD A. TRAVNICEK

It is certified that error appears in the above-indentified patent and that said Letters Patent is hereby corrected as shown below:

Col. 5, line 43, delete "V", and insert --V-- immediately to the left of structure indicated below, as follows:

V 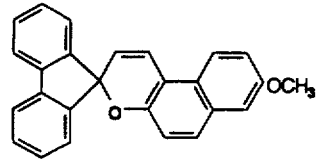

UNITED STATES PATENT AND TRADEMARK OFFICE
CERTIFICATE OF CORRECTION

PATENT NO. : 5,628,935
DATED : MAY 13, 1997
INVENTOR(S) : FRANK J. HUGHES, EDWARD A. TRAVNICEK

It is certified that error appears in the above-indentified patent and that said Letters Patent is hereby corrected as shown below:

Col. 14, lines 4-10, delete the following formula:

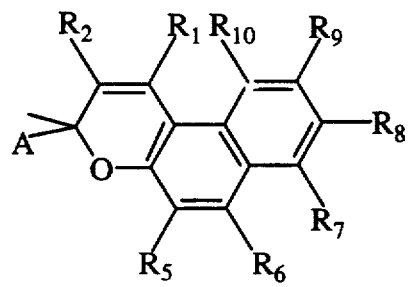

and insert the following formula under Col. 14, lines 4-10--

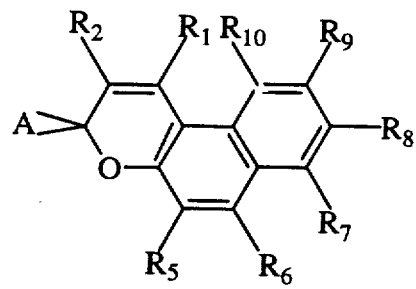

UNITED STATES PATENT AND TRADEMARK OFFICE
CERTIFICATE OF CORRECTION

PATENT NO. : 5,628,935
DATED : MAY 13, 1997
INVENTOR(S) : FRANK J. HUGHES, EDWARD A. TRAVNICEK

It is certified that error appears in the above-indentified patent and that said Letters Patent is hereby corrected as shown below:

Col. 15, lines 5-10, delete the following formula:

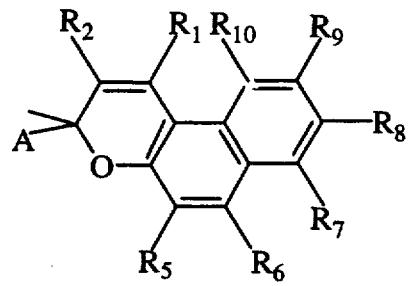

UNITED STATES PATENT AND TRADEMARK OFFICE
CERTIFICATE OF CORRECTION

PATENT NO. : 5,628,935
DATED : MAY 13, 1997
INVENTOR(S) : FRANK J. HUGHES, EDWARD A. TRAVNICEK

It is certified that error appears in the above-indentified patent and that said Letters Patent is hereby corrected as shown below:

and insert the following formula under Col. 15, lines 5-10--

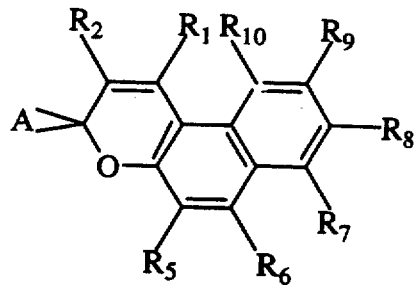

Signed and Sealed this

Twenty-fifth Day of November, 1997

Attest:

BRUCE LEHMAN

*Attesting Officer*     Commissioner of Patents and Trademarks